United States Patent [19]

Monflier et al.

[11] Patent Number: 5,345,007
[45] Date of Patent: Sep. 6, 1994

[54] PROCESS FOR THE PREPARATION OF OCTADIENOLS

[75] Inventors: Eric Monflier, Lille; Paul Bourdauducq, Chaponost; Jean-Luc Couturier, Lyons, all of France

[73] Assignee: Elf Atochem S.A., Puteaux, France

[21] Appl. No.: 148,257

[22] Filed: Nov. 5, 1993

[30] Foreign Application Priority Data

Nov. 6, 1992 [FR] France .................... 92 13392
Mar. 4, 1993 [FR] France .................... 93 02524

[51] Int. Cl.$^5$ .................... C07C 29/03; C07C 33/02
[52] U.S. Cl. .................... 568/909.5; 585/508
[58] Field of Search .................... 568/909.5

[56] References Cited

U.S. PATENT DOCUMENTS

| | | | |
|---|---|---|---|
| 3,407,224 | 10/1968 | Smutny | 568/909.5 |
| 3,670,032 | 6/1972 | Romanelli | 568/909.5 |
| 4,142,060 | 2/1979 | Kuntz . | |
| 4,219,677 | 8/1980 | Kuntz . | |
| 4,260,750 | 4/1981 | Kuntz . | |
| 4,927,960 | 5/1990 | Maeda et al. . | |
| 4,962,243 | 10/1990 | Roeper et al. | 568/909.5 |
| 4,990,698 | 2/1991 | Wada et al. | 568/909.5 |
| 4,992,609 | 2/1991 | Maeda et al. . | |
| 5,043,487 | 8/1991 | Thome et al. . | |
| 5,057,631 | 10/1991 | Tokitoh et al. | 568/909.5 |
| 5,100,854 | 3/1992 | Maeda et al. . | |
| 5,118,885 | 6/1992 | Tokitoh et al. . | |

FOREIGN PATENT DOCUMENTS

| | | | |
|---|---|---|---|
| 155795 | 6/1993 | Japan | 568/909.5 |
| 1354507 | 5/1974 | United Kingdom | 568/909.5 |

*Primary Examiner*—Joseph E. Evans
*Attorney, Agent, or Firm*—Finnegan, Henderson, Farabow, Garrett and Dunner

[57] ABSTRACT

A process for the preparation of octadienols, comprising the hydrodimerization reaction of 1,3-butadiene with water in the presence of a transition metal in the metal form or in the form of a compound of the said metal, of a water-soluble tertiary or quaternary phosphorus-containing compound and of at least one nitrogen-containing compound selected from the group consisting of a tertiary amine and a quaternary ammonium salt of general formula (I) or (II):

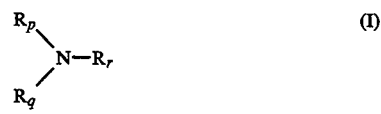

(I)

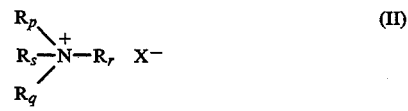

(II)

in which $R_p$, $R_q$ and $R_s$ are identical or different and each is a methyl or ethyl group; $R_r$ is an alkyl group containing from 6 to 22 carbon atoms; X is a counter-anion selected from the group consisting of $HCO_3^-$, $CO_3^{2-}$, $HSO_3^-$, $SO_3^{2-}$, $SiO_3^{2-}$, $PO_4^{3-}$, $HPO_3^{2-}$, $AsO_4^{3-}$, $SO_4^{2-}$, $HSO_4^-$, $RSO_3^-$, $RCO_2^-$, and $OH^-$, R being an alkyl group; the said reaction being carried out in the presence of carbon dioxide.

16 Claims, No Drawings

PROCESS FOR THE PREPARATION OF OCTADIENOLS

BACKGROUND OF THE INVENTION

1. Field of the Invention

The present invention relates to a process for the preparation of n-octadienols by dimerization and hydration of butadiene in the presence of a catalyst and of water.

2. Description of the Related Art

Many processes using such a hydrodimerization and leading to a mixture of octa-2,7-dien-1-ol and octa-1,7-dien-3-ol have been described in the prior art.

Octa-2,7-dien-1-ol is advantageous, in particular, as an intermediate for its hydrogenation to n-octan-1-ol, a product which is used in particular for the manufacture of plasticizers such as di-n-octyl phthalate.

French Patent 2,045,369 (which is a counterpart of GB 1,307,101A) describes a process for the preparation of these octadienols.

When the process of FP 2,045,369 is put into practice, a reaction mixture containing 1,3-butadiene, water and a solvent in which the butadiene and water are at least partially soluble is formed in the presence of a catalyst containing transition metal (palladium or platinum) compounds and a phosphine and of a cocatalyst consisting of carbon dioxide. The phosphine is chosen from known, water-insoluble compounds such as trialkylphosphines, triarylphosphines or tertiary alkylarylphosphines.

The solvent is chosen from dialkyl ethers, cyclic ethers, lower alkyl ethers of polyalcohols or of polyoxyalkylene glycols, alkyloxy- and aryloxypolyalkenoxyalcohols, ketones, amides, pyridine derivatives, sulphoxides, sulphones such as sulpholane, esters, aromatic solvents, aliphatic hydrocarbons or olefins.

Compounds known for reacting with the metal can be added to the reaction mixture. These compounds can be used as additional protection for preventing the deposition of metal during the reaction and during the subsequent treatment for the preparation of the catalyst with a view to recycling.

These compounds are listed in a list of more than 50 nitrogen-containing products comprising, inter alia, trimethylamine, triethylamine, tri-n-octylamine and dimethyldodecylamine.

Tests No. 11, 12 and 17 of Table VII of the above-mentioned patent, carried out in the presence of acetone and with or without triethylamine, the other factors remaining constant, show that the addition of triethylamine reduces both the octadienols yield, which falls from 75% to 70% and then to 42%, and also the selectivity of the formation of octa-2,7-dien-1-ol with respect to octa-1,7-dien-3-ol (89/11, 76/24, 73/27). On the other hand, the yield of octatriene, an undesired byproduct, increases and rises from 2% to 9% and then to 15%.

No experimental test using dimethyldodecylamine is described, and nothing suggests that this amine would be less unfavorable than triethylamine.

French Patent 2,366,237 (which is a counterpart of U.S. Pat. Nos. 4,142,060, 4,219,677, and 4,260,750) describes a family of water-soluble tertiary arylphosphines of general formula (A):

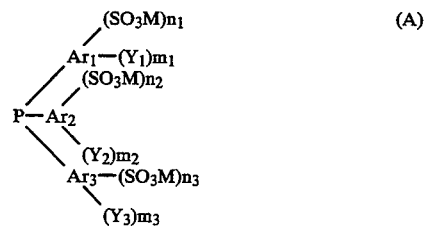

This solubility is brought about by the presence of at least one sulphonate group, M being a cationic residue of inorganic or organic origin.

This patent discloses a process for the hydrodimerization of butadiene in the presence of water and of a catalyst consisting of at least one of these soluble phosphines and of a transition metal in the metal form or in the form of a compound of the said metal chosen from Pd, Ni, Pt, Co or Rh, the said catalyst dissolving in the said water.

In order to considerably accelerate the reaction between butadiene and water, certain water-soluble compounds are added. These are alkali metal carbonates and bicarbonates, such as sodium carbonate and bicarbonate, sodium silicate and alkali metal salts of phosphorous, phosphoric and arsenic acid.

This process can also be implemented in the presence of aliphatic or aromatic tertiary amines.

Examples 7 to 16, relating to the synthesis of octadienols, without the presence of either tertiary amine or of solvent, show, Example 10 being the best, a degree of conversion of 76% and a selectivity of 64% towards octa-2-7-dien-1-ol and of 20% for octa-1,7-dien-3-ol from the butadiene consumed, i.e. a 1-ol/(1-ol+3-ol) selectivity equal only to 76% (100×64/84).

French Patent 2,479,187 (which is a counterpart of U.S. Pat. No. 4,356,333) proposes a process for the synthesis of n-octadienols in which butadiene and water are reacted in an aqueous sulpholane solution having a water/sulpholane ratio by weight with a value of 20/80 to 70/30 and containing carbonate and/or bicarbonate ions in the presence of:

(1) palladium or of a palladium compound;
(2) a unidentate phosphine of formula (B)

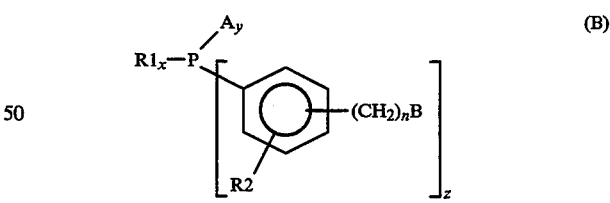

with the meanings of the terms as shown in this patent; and
(3) a unidentate tertiary amine having a basicity constant (pKa) of 7 or more, in an amount of 1 to 50% by volume based on the sulpholane.

This patent shows that butadiene can be replaced by a "$C_4$ fraction" but that preferably a butadiene of polymerization quality or a butadiene of chemical reaction quality are reacted, in view of the reaction rate and of the ease of recovery of the unreacted butadiene.

It is specified in French Patent 2,479,187 that useful unidentate amines comprise (lower) trialkylamines such as trimethylamine, triethylamine, tri-n-propylamine or tri-n-butylamine. Triethylamine is preferred on the basis of the yield of the reaction and of its intrinsic properties such as boiling point, solubility and cost.

Examples 3 and 7 of Table 2 of FR 2,479,187 show that the replacement of triethylamine by tri-n-propylamine causes a lowering in octadienols yield.

The presence of sulpholane in this process is a compromise between the advantages and the disadvantages brought about by this presence. In fact, it is shown that a sulpholane concentration of less than 30% by weight gives a significant reduction in the reaction rate. This is illustrated by Example 14 of this same Table 2 which shows that, in the presence of a water concentration of 90% by weight and of triethylamine, the amount of octadienols obtained from 25 g of butadiene (462 mmol) is only 1 mmol.

On the other hand, a sulpholane concentration exceeding 80% by weight leads not only to a reduction in the efficiency of extraction of the octadienols from the reaction mixture after the end of the reaction but also to an increase in the amounts of palladium and phosphine dissolved in the organ extraction phase and to an increase in the amounts of reaction byproducts.

Patent Application EP 0,296,550 (which is a counterpart of U.S. Pat Nos. 4,927,960, 4,992,609 and 5,100,854) discloses a process for the preparation of n-octadienols which is similar to the above, in which the unidentate phosphine of general formula (A) is replaced by a phosphonium salt of general formula (C):

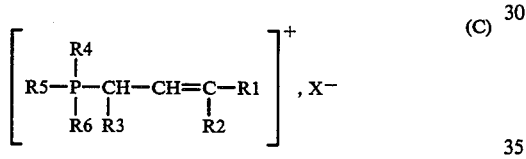

the substituents R1 to R6 having the meanings shown in this above application, x representing a hydroxyl, hydroxycarbonyloxy or lower alkylcarbonyloxy group.

This process is implemented with a reaction mixture containing a solvent, in particular sulpholane, and as shown in Examples 7 to 11 and 14 and 15, triethylamine and carbon dioxide.

Patent Application EP 0,411,410 (which is a counterpart of U.S. Pat. No. 5,043,487) dealing with the reaction of 1,3-butadiene with water in the presence of a triorganophosphine oxide, states that an economically very advantageous way of carrying out this reaction comprises using $C_4$ cuts in place of pure butadiene. The olefins 1-butene, 2-butene and isobutene additionally contained in the $C_4$ cut neither take part in the reaction nor are detrimental to it.

The $C_4$ cuts contain, by weight, approximately 45% of 1,3-butadiene, 17% of 1-butene, 10% of 2-butene, 25% of isobutene, the remainder being butane and isobutane.

Patent Application EP 0,436,226 (which is a counterpart of U.S. Pat. No. 5,118,885) teaches that the processes disclosed by U.S. Pat Nos. 4,356,333 and 4,417,079 have disadvantages during their continuous implementation on the industrial scale.

In fact, the components of the catalyst, namely palladium, phosphine, tertiary amine and also the solvent (sulpholane), are eluted in the extract obtained during the separation by extraction of the octadienols from the reaction mixture. When this extract is distilled, the palladium metal precipitates and finishes by fouling the distillation reboiler.

The technical solution proposed in this prior art consists in replacing the phosphine by a phosphonium salt of general formula (C) and in carrying out washings of the organic extraction phase with an aqueous sulpholane solution containing a water-soluble phosphine. This latter treatment complicates the industrial process for the synthesis of 1-octadienol.

An object of the present invention is to find an industrial process for the preparation of octadienols with a degree of conversion and/or an octadienols yield and/or selectivities towards octadienols and octa-2,7-dien-1-ol which are in the region of or higher than those of the prior art by using a particularly stable catalyst which is easy to recycle.

SUMMARY OF THE INVENTION

The solution to this problem lies in a process for the preparation of octa-2,7-dien-1-ol comprising the hydrodimerization reaction of 1,3-butadiene with water in the presence of a transition metal in the metal form or in the form of a compound of the said metal, of a water-soluble tertiary or quaternary phosphorus-containing compound and of at least one nitrogen-containing compound selected from the group consisting of a tertiary amine and a quaternary ammonium salt of general formula (I) or (II):

in which $R_p$, $R_q$ and $R_s$ are identical or different and each is a methyl or ethyl group; $R_r$ is an alkyl group containing from 6 to 22 carbon atoms; X is a counteranion selected from the group consisting of $HCO_3^-$, $CO_3^{2-}$, $HSO_3^-$, $SO_3^{2-}$, $SiO_3^{2-}$, $PO_4^{3-}$, $HPO_3^{2-}$, $AsO_4^{3-}$, $SO_4^{2-}$, $HSO_4$, $RSO_3^-$, $RCO_2^-$ and $OH^-$, wherein R is an alkyl group; said reaction being carried out in the presence of carbon dioxide.

DETAILED DESCRIPTION OF THE PREFERRED EMBODIMENTS

Preferably, the counteranion is selected from the group consisting of $HCO_3^-$, $CO_3^{2-}$, $RCO_2^-$ and $OH^-$.

The 1,3-butadiene reacted can be virtually pure (98% or more by weight) or form part of a mixture consisting of a $C_4$ cut or of a $C_4H$ cut used as such in the said hydrodimerization reaction. The $C_4H$ cut results from the removal from the $C_4$ cut of the acetylenic compounds by their selective hydrogenation.

In the context of the present invention, it was found that the $C_4$ or $C_4H$ cut each led to better yields of and selectivities towards octadienols than the virtually pure 1,3-butadiene reacted without the presence of an auxiliary solvent.

The transition metal is chosen from palladium, nickel, platinum, cobalt and rhodium. It can be in various oxidation states. Preferably, the transition metal is palladium.

Likewise, the transition metal compound is chosen from the compounds of metals comprising palladium, nickel, platinum, cobalt and rhodium, which are water-soluble or capable of dissolving under the conditions of the reaction, as is reported in Patent FR 2,366,237, with or without a reducing agent such as NaBH$_4$, Zn powder, magnesium, KBH$_4$ or hydrazine. Preferably, the transition metal compound is a palladium compound.

The specific choice of a tertiary amine of formula (I) or of a quaternary ammonium salt of formula (II) makes it possible to avoid the addition to the reaction mixture of an at least partially water-miscible solvent, in particular of sulpholane.

According to the present invention, it is nevertheless possible to add such a hydrophilic solvent to the reaction mixture, in particular a polar aprotic solvent such as dimethylformamide (DMF), dimethyl sulphoxide, acetonitrile, sulpholane or one chosen from polyethylene glycol ethers, for example tetraglyme.

However, the reaction of butadiene and of water is advantageously carried out without a water-miscible, or partially water-miscible solvent.

In fact, this absence of hydrophilic solvent during the reaction makes it possible to simplify the postreaction treatment leading to the isolation of the octadienols.

On the other hand, it was found that the hydrodimerization reaction of the virtually pure butadiene was promoted by the presence of a monoethylenic or saturated hydrocarbon having from 4 to 7 carbon atoms. This water-immiscible hydrocarbon moreover promotes the subsequent treatment of the reaction mixture after the end of the hydrodimerization reaction. This hydrocarbon can have a linear, branched or cyclic carbon skeleton. It can be in particular butane, pentane, cyclopentane, hexane, cyclohexane, heptane or their monoethylenic homologues.

The tertiary or quaternary phosphorus-containing compound can be a phosphine or a phosphonium salt of general formula (A), (B) or (C) above and such as described in the prior art.

This compound can thus be a triarylphosphine substituted by at least one sulphonate group of an alkali metal such as sodium, potassium or lithium. The counteranion of the sulphonate group can also be chosen from quaternary ammonium groups.

The amines of general formula (I) and the quaternary ammoniums of formula (II) have R$_p$, R$_q$ and, if appropriate, R$_s$ groups which each represent, independently of one another, a methyl or ethyl group.

Preferably, R$_p$, R$_q$ and, if appropriate, R$_s$ each represent a methyl group.

The amine (I) can be dissolved in water by salification using an acid, in particular carbon dioxide (CO$_2$).

Some of these amines (I) are commercially available, either pure or as mixtures.

Generally, the amines (I) can be synthesized by alkylation of a diamine of formula R$_r$R$_q$NH using an alkylating agent of formula R$_r$X, X being a leaving group, for example halogen.

The amines (I) can also be obtained from the primary amine R$_r$—NH$_2$ by reaction with formaldehyde or with acetaldehyde and catalytic hydrogenation.

Some of these quaternary ammonium salts (II) are commercially available. If these salts have a halide, in particular Cl$^-$, Br$^-$, I$^-$ or F$^-$, as counter-anion, the said halide is changed beforehand, for example using an ion-exchange resin, to another counter-anion belonging to the abovementioned family, in order not to inhibit the hydrodimerization reaction.

Generally, the salts (II) can be prepared conventionally by alkylation of the tertiary amine (I) with an alkylating agent of formula R-Z, Z being a leaving group, in particular halide or sulphate. The alkylating agents can be, for example, dimethyl sulphate or diethyl sulphate.

The reaction according to the invention can be carried out using an amine or a mixture of amines (I) or an ammonium salt (II) or a mixture of salts (II).

The alkyl group R$_r$ preferably represents the radical —(CH$_2$)$_n$CH$_3$ in which n has the value of an integer between 5 and 21.

Advantageously, n is an integer between 9 and 17, especially 11.

Preferably, the reaction is carried out at a temperature between 20° and 100° C.

After the end of the reaction, the reaction mixture is, if necessary, placed at ambient pressure and temperature. The reaction mixture is subjected directly to a flash distillation. The organic phase collected is then rectified by distillation. The residue from the first flash distillation, essentially comprising the phosphorus-containing compound, the transition metal and the tertiary amine (I) or the ammonium salt (II), can be recycled in a new reaction with butadiene and water.

In addition to the preceding description, the following examples, given purely by way of illustration, make it possible better to understand the present invention.

In these examples, the products were identified by $^{13}$C NMR using an AC 300 Bruker apparatus, by IR spectrum on a Nicolet 20 SXB, by mass spectrography using a Fison VG 12250 and by gas phase chromatography on a silicone column with n-octanol as internal standard.

The autoclave used is the 100 ml or 300 ml "Autoclave Engineer" model.

The palladium (II) acetate (Aldrich) has a purity of 98%.

The 1,3-butadiene (Union Carbide) has a purity greater than 99%. Among the abbreviations used:

TPPTS is the trisodium salt of tri(metasulphophenyl)-phosphine. This salt is prepared experimentally according to French Patent 2,366,237.

TPPMS is the monosodium salt of (metasulphophenyl) diphenylphosphine. This salt is prepared according to Arhland et al., Journal of the Chemical Society, 276–288 (1958).

Noram DMCD represents dimethyl cocoamine, the coconut radical being a mixture of saturated linear C$_8$ (4%), C$_{10}$ (6%), C$_{12}$ (55%), C$_{14}$ (18%), C$_{16}$ (10%) and C$_{18}$ (7%) alkyl groups.

Noram DMSHD represents dimethyl hydrogenated tallow amine hydrogenated tallow means a mixture of saturated linear C$_{12}$ (0.1%), C$_{14}$ (0.9%), C$_{16}$ (28%) and C$_{18}$ (71%) alkyl groups.

Noram MC$_2$ represents methyl dicocoamine.

These Noram products are commercially available from the Company Ceca/Elf Atochem (France).

The C$_4$ and C$_4$H cuts have the following compositions by weight, shown in Table I below:

TABLE I

|  | C$_4$ | C$_4$H |
|---|---|---|
| Cyclopropane | 0.04 | 0.02 |
| Propylene | — | 0.04 |
| Isobutane | 0.57 | 0.91 |
| Propadiene | 0.02 | 0.01 |
| n-Butane | 3.02 | 4.61 |
| Unidentified | 0.03 | 0.03 |
| trans-2-Butene | 5.06 | 6.55 |

TABLE I-continued

|  | C₄ | C₄H |
|---|---|---|
| 1-Butene | 12.32 | 15.13 |
| Isobutene | 26.98 | 27.15 |
| cis-2-Butene | 4.08 | 4.47 |
| Butadiene | 0.30 | 0.14 |
| Propyne | 0.02 | — |
| 1,3-Butadiene | 46.71 | 40.91 |
| Vinylacetylene | 0.69 | — |
| Ethylacetylene | 0.16 | — |
| Total | 100.0 | 99.97 |

In the following examples:
The total reaction time is equal to the time for which the autoclave has been heated.
The temperature is °C. is that of the autoclave, measured using a calibrated thermocouple.
The degree of conversion, in %, is equal to the ratio multiplied by 100 of the number of moles of butadiene consumed to the number of moles of butadiene introduced into the autoclave.
The octadienols yield, in %, is equal to the ratio multiplied by 100 of the number of moles of butadiene converted to octadienols to the number of moles of butadiene introduced.
The selectivity towards octadienols, in %, is equal to the ratio multiplied by 100 of the number of moles of butadiene converted to octadienols to the number of moles of butadiene consumed.
The selectivity towards 1-ol/ols, in %, is equal to the ratio multiplied by 100 of the number of moles of 1-octadienol to the number of moles of 1- and 3-octadienols.
The dimers yield, in %, is equal to the ratio multiplied by 100 of the number of moles of butadiene converted to dimers to the number of moles of butadiene introduced.
The dimers consist essentially of vinylcyclohexene and of octatrienes.
The dioctadienyl ethers result from the dehydration of the octadienols.
The ethers yield, in %, is equal to the ratio multiplied by 100 of the number of moles of butadiene converted to ethers to the number of moles of butadiene introduced.
The expression "various products- represents unidentified products.

Example 1

0.146 g (6.5·10⁻⁴ mol) of palladium acetate (Pd(OAc)₂), 1.25 g (2·10⁻³ mol) o TPPTS, 6.5 g (0.03 tool) of dimethyldodecylamine, 12 g (0.666 mol) of H₂O and 18 g (0.333 mol) of butadiene were introduced, under an argon atmosphere, into a 100 ml, stainless steel autoclave equipped with a mechanical stirrer.
The autoclave was then pressurized under 10 bar of CO₂.
The temperature of the autoclave was progressively raised to 85° C. over a time of 15 min while stirring the reaction mixture at 800 revolutions/minute. The reaction was continued at 85° C. for 30 min.
The reaction was followed by monitoring the reduction in the pressure inside the autoclave.
When the pressure was no longer changing, the autoclave was cooled to room temperature and was then degassed by opening the valve. The crude reaction mixture, collected under a CO₂ atmosphere, comprised two phases: a supernatant organic phase above an aqueous phase. The organic phase, analyzed by chromatography, showed an octadienols yield of 72% (67% octa-2,7-dien-1-ol, 5% octa-1,7-dien-3-ol), a mixture of octatriene and of vinylcyclohexene yield of 17% and a dioctadienyl ethers yield of 3%. The selectivity towards 1-ol/ols was 93%.

Examples 2–9

The experimental conditions of Example 1 were repeated as shown in the following Table II, which illustrates eight other solvent-free implementational examples of the process according to the invention. The molar amounts of reactants were the same as those in Example 1 except if otherwise specified.
In Example 3, part of the crude reaction mixture was stored for 1 month at room temperature under a CO₂ atmosphere. It then showed no black precipitate, a sign of decomposition of the catalyst.

Examples 10–12

Table III shows Examples 10 and 12 according to the present invention and comparative Example 11, carried out in the presence of solvent (sulpholane). The amounts of sulpholane and the molar amounts of reactants used were those of the first example of French Patent 2,479,187 multiplied by 1.5. A 300 ml autoclave of the type shown above was used. By way of comparison, Example 11 was repeated three times (mean of the three tests carried out). All the three crude reaction mixtures of this Example 11 already contained a black precipitate, a sign of decomposition of the catalyst, when they were taken out of the autoclave.

Examples 13–21

The results of Example 10 are better than those of Example 11.
Table IV shows 10 comparative examples (Nos. 13 to 21) carried out without solvent and with the same molar amounts of reactants as Example 1 of Table I, with the exception of the amounts of amine or of potassium carbonate, equal to 0.01 mol.
For the same molar amount of amine, Examples 4 to 9 lead to a higher degree of conversion and/or to a higher octadienols yield and/or to higher selectivities than the Comparative Examples 15 to 21.

Example 22

0.30 g (1.35 mmol) of palladium acetate (Pd(OAc)₂), 2.4 g (4.2 mmol) of TPPTS, 23.4 g (105 mmol) of dimethyldodecylamine, 25.2 g (1.4 tool) of H₂O and 80.9 g of C₄ cut containing 37.8 g (700 mmol) of butadiene were introduced, under an argon atmosphere, into a 300 ml, stainless steel autoclave equipped with a mechanical stirrer. The autoclave was then pressurized under 10 bar of CO₂.
The temperature of the autoclave was progressively raised to 70° C. over a time of 30 minutes while stirring the reaction mixture at 800 revolutions/minute.
The reaction was continued at 70° C. for 150 minutes.
The autoclave was cooled to room temperature and then degassed.
The crude reaction mixture, collected under a CO₂ atmosphere, comprised two phases: a supernatant organic phase above an aqueous phase.
The organic phase was analyzed by chromatography and the results appear in Table V below.

Examples 23–31

Table V shows, in addition to Example 22, nine other Examples 23 to 31.

The operating conditions were the same as those of Example 22 and, in particular, the molar amounts of reactants were identical to those in Example 22, except if otherwise specified.

In Examples 22, 23, 25 to 28, 30 and 31, the $C_4$, $C_4H$, butadiene and pentane, and butadiene and 1-pentene mixtures each contained the same amount of 1,3-butadiene (700 mmol) as Examples 24 and 29, carried out with 99% pure butadiene.

These mixtures gave better results in terms of degree of conversion, octadienols yields and selectivity towards octadienols than pure 1,3-butadiene.

Example 32
Preparation of cetyltrimethylammonium hydroxide.

Cetyltrimethylammonium bromide (Aldrich) was dissolved in water at a concentration of approximately 0.2 mol/liter and then this solution was passed through an Amberlite IRA 420 (OH) ion-exchange column. The solution collected was concentrated under vacuum until a gel formed.

Analysis showed that the $Br^-$ ions were completely exchanged and replaced by OHM ions to give an 18% by weight, with respect to the weight of the solution, cetyltrimethylammonium hydroxide solution.

Example 33

0.44g ($1.96 \cdot 10^{-3}$ mol) of palladium acetate ($Pd(OAc)_2$), 2.13 g ($5.85 \cdot 10^{-3}$ mol) of TPPMS, 81 g (4.5 mol) of water, 54 g (1 mol) of 1,3-butadiene and 18.1 g(0.06 mol) of cetyltrimethylammonium hydroxide (formula (II): $R_r = -n - C_{16}H_{33}$, $R_p = R_q - CH_3$, $X - OH^-$) were introduced, under an argon atmosphere, into a 300 ml stainless steel autoclave equipped with a mechanical stirrer.

The autoclave was then pressurized under 10 bar of carbon dioxide. The temperature of the autoclave was raised to 70° C. and the reaction was then left for 90 minutes at this temperature, the reaction mixture being stirred throughout at 800 revolutions/minute. After returning to room temperature, the autoclave was degassed. The crude reaction mixture collected comprised two phases: a supernatant organic phase and an aqueous phase. The organic phase was analyzed by gas phase chromatography as shown above.

Comparative Example 34

This example was carried out in a manner identical to Example 33, except that cetyltrimethylammonium hydroxide was replaced by the same molar amount of tetramethylammonium hydroxide.

The results obtained appear in Table VI below.

TABLE II

| Example No. | Additives | Phosphine | Total reaction time in minutes | Temperature in °C. | Solvent-free Degree of conversion in % | Octadienols yield in % | Selectivity towards octadienols in % | Selectivity towards 1-01/ols in % | Dimers yield in % | Dioctadienyl ethers yield in % |
|---|---|---|---|---|---|---|---|---|---|---|
| 1 | $CO_2$ Dimethyldodecylamine | TPPTS | 45 | 85 | 92 | 72 | 79 | 93 | 17 | 3 |
| 2 | $CO_2$ Dimethyldodecylamine | TPPTS[b] | 240 | 55 | 95 | 76 | 80 | 96 | 17 | 2 |
| 3 | $CO_2$ Dimethyldodecylamine[c] | TPPTS | 45 | 70 | 85 | 69 | 81 | 93 | 16 | traces |
| 4 | $CO_2$ Dimethylhexylamine[d] | TPPTS | 90 | 85 | 89 | 63 | 71 | 94 | 16 | 8 |
| 5 | $CO_2$ Dimethyldodecylamine[d] | TPPMS | 90 | 85 | 66 | 56 | 85 | 91 | 7 | 3 |
| 6 | $CO_2$ Dimethyloctylamine[d] | TPPMS | 90 | 85 | 65 | 54 | 83 | 90 | 5 | 6 |
| 7 | $CO_2$ Noram DMCD[d] | TPPTS | 90 | 85 | 85 | 59 | 70 | 94 | 15 | 8 |
| 8 | $CO_2$ Noram DMCD[d] | TPPMS | 90 | 85 | 81 | 65 | 80 | 91 | 10 | 6 |
| 9 | $CO_2$ Noram DMSHD[d] | TPPTS | 90 | 85 | 86 | 62 | 72 | 94 | 15 | 8 |

[b] $1.33 \cdot 10^{-3}$ mol of TPPTS
[c] 0.05 mol of amine
[d] 0.01 mol of amine

TABLE III

| Example No. | Additives | Phosphine | Total reaction time in minutes | Temperature in °C. | In the presence of Sulpholane Degree of conversion in % | Octadienols yield in % | Selectivity towards octadienols in % | Selectivity towards 1-01/ols in % | Dimers yield in % | Dioctadienyl ethers yield in % |
|---|---|---|---|---|---|---|---|---|---|---|
| 10 | $CO_2$ Dimethyldodecylamine | TPPMS | 195 | 85 | 61 | 47 | 77 | 95 | 14 | 0.4 |
| 11* | $CO_2$ $N(Et)_3$ | TPPMS | 195 | 85 | 44 | 33 | 76 | 94 | 10 | 0.2 |
| 12 | $CO_2$ Dimethyldodecylamine | TPPTS | 195 | 85 | 66 | 49 | 74 | 95 | 15 | 0.4 |

*Comparative example

TABLE IV

| Example No. | Additives | Phosphine | Total reaction time in minutes | Temperature in °C. | Solvent-free Degree of conversion in % | Octadienols yield in % | Selectivity towards octadienols in % | Selectivity towards 1-ol/ols in % | Dimers yield in % | Dioctadienyl ethers yield in % |
|---|---|---|---|---|---|---|---|---|---|---|
| 13* | K$_2$CO$_3$ | TPPTS | 195 | 85 | 26 | 20 | 77 | 70 | 6 | — |
| 14* | CO$_2$ | TPPTS | 195 | 85 | 6 | traces | — | — | 5 | — |
| 15* | CO$_2$ N(Et)$_3$ | TPPTS | 195 | 85 | 11 | 5 | 50 | 82 | 5 | — |
| 16* | CO$_2$ N(n-Bu)$_3$ | TPPTS | 195 | 85 | 7 | 1 | 14 | 46 | 6 | — |
| 17* | CO$_2$ N(Et)$_3$ | TPPMS | 90 | 85 | 33 | 20 | 60 | 85 | 10 | 3 |
| 18* | CO$_2$ Dimethylbutylamine | TPPMS | 90 | 85 | 28 | 22 | 79 | 91 | 5 | 1 |
| 19* | CO$_2$ N(n-Bu)$_3$ | TPPMS | 90 | 85 | 22 | 12 | 54 | 25 | 10 | — |
| 20* | CO$_2$ N(n-Octyl)$_3$ | TPPMS | 90 | 85 | 17 | 1 | 6 | — | 10 | — |
| 21* | CO$_2$ Noram MC$_2$ | TPPTS | 195 | 85 | 4 | — | — | — | 4 | — |

*Comparative examples
Additives: K$_2$CO$_3$ or Amine = 0.01 mol

TABLE V

| Example No. | Phosphine | 1,3-Butadiene used in the form of: | Degree of conversion in % | Octadienols yield in % | Selectivity towards octadienols in % | Selectivity towards 1-ols in % | Dimers yield in % | Ethers yield in % | Yield of various products in % |
|---|---|---|---|---|---|---|---|---|---|
| 22 | TPPTS | C$_4$ | 87.8 | 70.6 | 80.4 | 92.4 | 9.3 | 3.1 | 4.8 |
| 23 | TPPTS | C$_4$H | 89.0 | 73.7 | 82.8 | 91.7 | 7.9 | 3.4 | 4.0 |
| 24 | TPPTS | 1,3-butadiene | 74.6 | 55.4 | 74.3 | 92.8 | 15.1 | 2.1 | 2.0 |
| 25 | TPPTS | 1,3-butadiene + pentane$^{(a)}$ | 87.9 | 70.3 | 80.0 | 91.5 | 8.9 | 3.2 | 5.5 |
| 26 | TPPMS | C$_4$ | 95.6 | 73.6 | 77.0 | 86.4 | 11.8 | 3.5 | 6.7 |
| 27 | TPPMS | C$_4$H | 86.4 | 67.5 | 78.1 | 82.7 | 9.3 | 3.5 | 6.1 |
| 28 | TPPMS | C$_4$H$^{(b)}$ | 71.7 | 57.8 | 80.6 | 86.7 | 4.8 | 3.6 | 5.5 |
| 29 | TPPMS | 1,3-butadiene | 81.4 | 54.6 | 67.1 | 79.1 | 15.4 | 3.4 | 8.0 |
| 30 | TPPMS | 1,3-butadiene + pentane$^{(c)}$ | 94.4 | 68.3 | 72.3 | 80.5 | 14.3 | 5.0 | 6.8 |
| 31 | TPPMS | 1,3-butadiene + 1-pentene$^{(d)}$ | 92.5 | 66.5 | 71.9 | 79.1 | 15.2 | 4.7 | 6.1 |

$^{(a)}$pentane = 54.5 g
$^{(b)}$0.042 mol of C$_{12}$H$_{25}$N(CH$_3$)$_2$ amine
$^{(c)}$pentane = 60.4 g
$^{(d)}$pentene = 54.1 g

TABLE VI

| Example No. | Phosphine | 1,3-Butadiene used in the form of: | Degree of conversion in % | Octadienols yield in % | Selectivity towards octadienols in % | Selectivity towards 1-ol/ols in % | Dimers yield in % | Ethers yield in % | Yield of various products in % |
|---|---|---|---|---|---|---|---|---|---|
| 33 | TPPMS | 1,3-butadiene | 84 | 60 | 71 | 90 | 7 | 13 | 4 |
| 34* | TPPMS | 1,3-butadiene | 16 | 9 | 56 | 89 | 4 | 2 | 1 |

*Comparative example

We claim:

1. A process for the preparation of an octa-2,7-dien-1-ol comprising hydrodimerizing 1,3-butadiene with water in the presence of:
   a transition metal in the metal form or in the form of a compound of the said metal;
   a water-soluble tertiary or quarternary phosphorus-containing compound; and
   at least one nitrogen-containing compound, selected from the group consisting of a tertiary amine and a quaternary ammonium salt of formula (I) or (II):

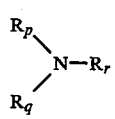
(I)

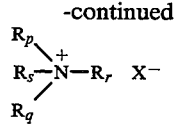
(II)

in which $R_p$, $R_q$ and $R_s$ are identical or different and each is a methyl or ethyl group; $R_r$ is an alkyl group containing from 6 to 22 carbon atoms; X is a counter-anion selected from the group consisting of: HCO$_3^-$, CO$_3^{2-}$, HSO$_3^-$, SO$_3^{2-}$, SiO$_3^{2-}$, PO$_4^{3-}$, HPO$_3^{2-}$, AsO$_4^{3-}$, SO$_4^{2-}$, HSO$_4^-$, RSO$_3^-$, RCO$_2^-$, and OH$^-$,
wherein R is an alkyl group; said reaction being carried out in the presence of carbon dioxide.

2. A process according to claim 1, wherein the 1,3-butadiene has a purity equal to or greater than 98% by weight.

3. A process according to claim 1, wherein the 1,3-butadiene forms pan of a $C_4$ or $C_4H$ cut used as such in the said hydrodimerization reaction.

4. A process according to claim 1, wherein the said reaction of butadiene and water is carried out in the absence of a water-miscible or partially water-miscible solvent.

5. A process according to claim 2, wherein the said hydrodimerization reaction is carried out in the presence of a monoethylenic or saturated hydrocarbon having from 4 to 7 carbon atoms.

6. A process according to claim 3, wherein the transition metal is palladium.

7. A process according to claim 2, wherein the transition metal is palladium.

8. A process according to claim 1, wherein the transition metal is palladium.

9. A process according to claim 3, wherein the transition metal compound is a palladium compound.

10. A process according to claim 2, wherein the transition metal compound is a palladium compound.

11. A process according to claim 1, wherein the transition metal compound is a palladium compound.

12. A process according to claim 1, wherein $R_p$, $R_q$ and $R_s$ each is a methyl group.

13. A process according to claim 1, wherein $R_r$ is the radical $-(CH_2)_n CH_3$ in which n is an integer between 5 and 21.

14. A process according to claim 9, wherein n is between 9 and 17.

15. A press according to claim 10, wherein n is 11.

16. A process according to claim 1, wherein the said reaction is carried out at a temperature between 20° and 100° C.

* * * * *